United States Patent [19]  [11] 4,302,540
Hirata et al.  [45] Nov. 24, 1981

[54] PROCESS OF PRODUCING OPTICALLY ACTIVE CEPHALOSPORIN ANALOGS BY ENZYME SELECTIVE DEACYLATION

[75] Inventors: Tadashi Hirata, Yokohama; Yukio Hashimoto, Yamato; Takehiro Ogasa, Machida; Shigeru Kobayashi, Machida; Akira Sato, Machida; Kiyoshi Sato, Shizuoka; Seigo Takasawa, Hadano, all of Japan

[73] Assignee: Kyowa Hakko Kogyo Co., Ltd., Tokyo, Japan

[21] Appl. No.: 200,551

[22] Filed: Oct. 24, 1980

[30] Foreign Application Priority Data

Oct. 25, 1979 [JP] Japan .................................. 54-136986
Apr. 26, 1980 [JP] Japan .................................. 55-55618

[51] Int. Cl.³ ........................ C12P 17/18; C07B 19/02

[52] U.S. Cl. .................................... 435/119; 435/280; 435/822; 435/823; 435/824; 435/829; 435/830; 435/843; 435/848; 435/850; 435/859; 435/842; 435/870; 435/874; 435/873; 435/882; 435/886; 435/910; 435/911; 435/832

[58] Field of Search ................................ 435/119, 280

[56] References Cited

FOREIGN PATENT DOCUMENTS 55-114297 9/1980 Japan .................................. 435/119

OTHER PUBLICATIONS

Journal American Chemical Society vol. 96 pp. 7584–7585 (Nov. 1974).
Journal of Medicinal Chemistry vol. 20 pp. 551–556 (1977).

Primary Examiner—Lionel M. Shapiro
Attorney, Agent, or Firm—Fitzpatrick, Cella, Harper & Scinto

[57] ABSTRACT

Disclosed are optically active cephalosporin analogs which are produced by optically selective deacylation of an optically inactive acylated analog. The compounds are useful as intermediates in the preparation of optically active acylated antimicrobial agents.

4 Claims, No Drawings

PROCESS OF PRODUCING OPTICALLY ACTIVE CEPHALOSPORIN ANALOGS BY ENZYME SELECTIVE DEACYLATION

BACKGROUND OF THE INVENTION

The present invention relates to optically active cephalosporin analogs and, more particularly, it pertains to optically active compounds of cephalosporin analogs represented by the general formula (I)

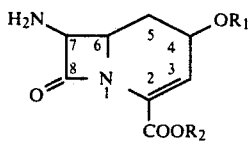

wherein $R_1$ represents a hydrogen, a lower alkyl group or a lower acyl group, $R_2$ represents a hydrogen or a protective group of carboxylic acid, and the hydrogens at the 6- and 7-positions have cis configuration, the salts thereof and processes for producing the same.

Heretofore, a carbacephem compound, which is named according to the nomenclature in J. Am. Chem. Soc. 96, 7584 (1974), wherein the sulfur atom of cephalosproin is substituted with a carbon atom and which has a substituted methyl group at the 3-position is described in the above reference and J. Med. Chem. 20, 551 (1977). However, no compound of this type having especially strong antibacterial activity has been reported.

The present inventors have succeeded in preparing carbacephem compounds having various substituents at the 4-, 5- and 3-positions [The numbering system is as shown in general formula (I)]. The compounds are described in the specifications of Japanese Published Unexamined Patent Application No. 128591/79, German Offenelegungsschrift No. 2911786, referred to as "G.O." hereinafter, and U.S. Patent Application Ser. No. 23,645 filed on Mar. 23, 1979.

Further, the present inventors have succeeded in preparing novel acylated carbacephems which are new antibiotics having strong antibacterial activities. These are described in Japanese Published Unexamined Patent Application No. 128591/79, G.O. 2911787 and U.S. Patent Application Ser. No. 23,646 filed on Mar. 23, 1979.

However, cephalosporin analogs mentioned above are prepared by synthetic methods using optically inactive starting compounds, and they are optically inactive dl [represented by (±)] compounds unless they have optically active acyl group. More specifically, compounds represented by the general formula (II)

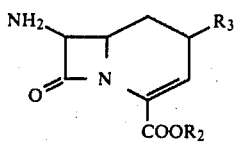

wherein $R_2$ has the same significance as defined above, $R_3$ represents a hydrogen, a lower alkyl group or a lower acyloxy group and the hydrogen atoms at the 6- and 7-positions have cis configuration are present as a mixture of equal amounts of the mirror image compounds represented by the formulae (II-1) and (II-2)

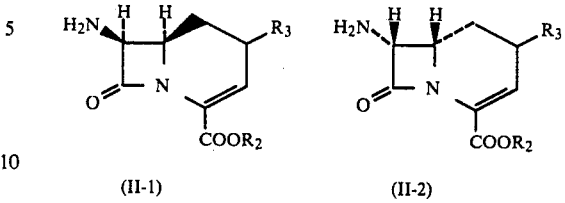

wherein $R_2$ and $R_3$ have the same significance as defined above.

As a result of various studies, the present inventors have succeeded in preparing and isolating one of the optically active mirror image compounds represented by the assumed formula (II-1), which is disclosed in Japanese Patent Application No. 14533/79 (European Patent Application 80100663.6)

Similarly, compounds represented by the general formula (I) wherein the hydrogen atoms at the 6- and 7-positions have cis configuration are also present as a mixture of equal amounts of the mirror image compounds represented by the formulae (I-1) and (I-2)

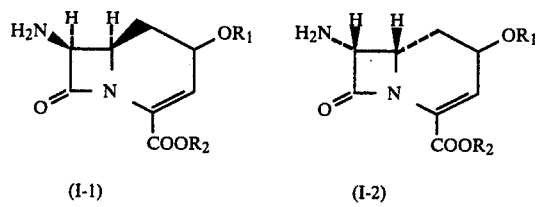

wherein $R_1$ and $R_2$ have the same significance as defined above.

As a result of further studies, the present inventors have also succeeded in preparing and isolating one of the optically active mirror image compounds represented by the formula (I-1).

SUMMARY OF THE INVENTION

In accordance with the present invention, optically active compounds are prepared of cephalosporin analogs represented by the formula:

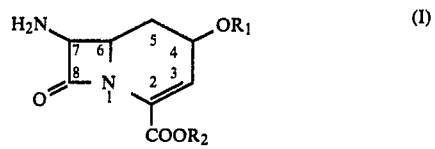

(wherein $R_1$ represents a hydrogen, a lower alkyl group or a lower acyl group, $R_2$ represents a hydrogen or a protective group of carboxylic acid and the hydrogens at the 6- and 7-positions have cis configuration) and salts thereof.

In the foregoing general formula (I), the lower alkyl group $R_1$ is a straight-chain or branched alkyl group having 1 to 5 carbon atoms such as methyl, ethyl, n-propyl, i-propyl, n-butyl, i-butyl, sec-butyl, t-butyl, and the like. The alower acyl group is represented by $R_3CO$ wherein $R_3$ is a straight-chain or branched alkyl group having 1 to 5 carbon atoms such as methyl, ethyl, n-propyl, i-propyl, n-butyl, i-butyl, sec-butyl, t-butyl, and the like.

The ester group COOR$_2$ is a group readily convertible to COOH employed in the chemistry of penicillins and cephalosporins.

The group R$_2$ may be a straight-chain or branched alkyl group having 1 to 5 carbon atoms such as methyl, ethyl, n-propyl, i-propyl, n-butyl, i-butyl, sec-butyl, t-butyl, and the like; a straight-chain or branched alkoxymethyl group having 1 to 5 carbon atoms such as methoxymethyl, ethoxymethyl, and the like; a straight-chain or branched halogenated alkyl group having 1 to 5 carbon atoms such as chloromethyl, 2,2,2-trichloroethyl, 2,2,2-trifluoroethyl, and the like; a lower alkylsulfonylethyl group such as methylsulfonylethyl, ethylsulfonylethyl, and the like; an arylmethyl group having 7 to 12 carbon atoms such as benzyl, diphenylmethyl, triphenylmethyl, and the like; a substituted arylmethyl group having 7 to 20 carbon atoms wherein the substituent is a methoxy group, a nitro group, or the like and the number of the substituents on the phenyl ring is 1 to 5; or a protective group of carboxylic acid represented by the general formula (III)

wherein R$_4$ represents a straight-chain or branched lower alkyl group having 1 to 5 carbon atoms, a straight-chain or branched lower alkoxy group having 1 to 5 carbon atoms, or a phenyl group, and R$_5$ represents a hydrogen or a straight-chain or branched lower alkyl group having 1 to 5 carbon atoms.

The optically active compounds of cephalosporin analogs represented by the general formula (I), that is, one of the enantiomers, are prepared, according to the present invention, by an optically selective deacylation reaction using an enzyme and an optically inactive dl compound having a certain acyl group as a starting compound. The desired compounds are obtained in a remarkably high yield by this method.

A compound wherein an optically active acyl group is introduced to a dl form of a compound represented by the general formula (II), referred to as Compound [II] hereinafter, that is, the compound represented by the general formula (IV)

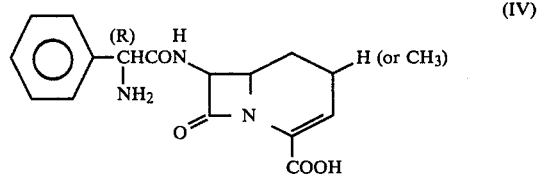

is separated to diastereoisomers (Japanese Published Unexamined Patent Application No. 128591/79, G.O. 2911787 and U.S. Patent Application Ser. No. 23646).

The optically active compounds obtained in the present invention are assumed to have the absolute structure represented by the general formula (I-1), that is (6R, 7S), from various properties, stronger antimicrobial activity of the acyl compounds compared with that of the corresponding optically inactive dl-compound and the relationship between the absolute structure of cephalosporins and activities thereof. These compounds are particularly useful as intermediates in the preparation of optically active acylated compounds which are strong antibacterial agents.

In the following description, the optically active compounds are described with reference to the general formula (I-1). Additionally, the compounds in the following examples and reference examples are named according to the assumed absolute structural formula.

DETAILED DESCRIPTION OF THE INVENTION

Optically active compounds of the cephalosporin analogs represented by the general formula (I) or compounds represented by the assumed absolute structural formula (I-1) are produced by optically selective deacylation of a compound represented by the general formula (V)

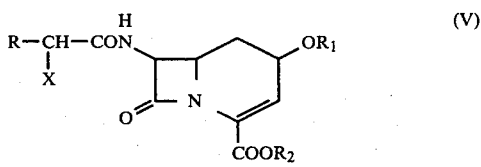

wherein R represents a substituted or unsubstituted unsaturated six-membered carbocycle, or a substituted or unsubstituted five- or six-membered heterocycle wherein the substituent represents a hydroxy group, a halo group, a nitro group or a methansulfonamide group, X represents a hydrogen, an amino group, a hydroxy group or a lower alkyl group, R$_1$ and R$_2$ have the same significance as defined above, and the hydrogens at the 6- and 7-positions have cis configuration (referred to as Compound [V] hereinafter).

As the unsaturated six-membered carbocycle and five- or six-membered heterocycle, a phenyl group, a cyclohexenyl group, a cyclohexadienyl group, a thienyl group, a furyl group, a pyrrolyl group, a thiazolyl group, an isothiazolyl group, an oxazolyl group, an iso-oxazolyl group, an imidazolyl group, a pyrazolyl group, a triazolyl group, a tetrazolyl group, a pyridinyl group, and a pyrazinyl group are exemplified. As the substituent, a hydroxy group, a halo group, a nitro group, a methansulfonamide group, and the like are mentioned. As the lower alkyl group, a straight-chain or branched alkyl group having 1 to 5 carbon atoms such as methyl, ethyl, n-propyl, i-propyl, n-butyl, i-butyl, sec-butyl, t-butyl and the like are mentioned.

The optically selective deacylation of Compound [V] to obtain optically active Compound [I-1] is carried out in the presence of an enzyme obtained from a microorganism capable of producing optically active Compound [I-1] by optically selective deacylation of Compound [V].

As the microorganism having the ability of optically selective deacylation, microorganisms belonging to the genus Aeromonas, Achromobacter, Arthrobacter, Acetobacter, Alcaligenes, Escherichia, Xanthomonas, Kluyvera, Gluconobacter, Clostridium, Comamonas, Corynebacterium, Sarcina, Staphylococcus, Spirillum, Bacillus, Pseudomonas, Flavobacterium, Brevibacterium, Protaminobacter, Proteus, Beneckea, Micrococcus, Mycoplana or Rhodopseudomonas are used. The following strains are examples of the microorganism.

| | | |
|---|---|---|
| 1. | *Aeromonas hydrophila* | IFO 12634 |
| 2. | *Achromobacter aceris* | IFO 3320 |

| | | |
|---|---|---|
| 3. | Arthrobacter simplex | ATCC 15799 |
| 4. | Acetobacter aurantius | IFO 3245, |
| 5. | Acetobacter sp. | ATCC 21760 |
| 6. | Alcaligenes faecalis | ATCC 8750 |
| 7. | Escherichia coli | ATCC 11105 |
| 8. | Escherichia coli | ATCC 13281 |
| 9. | Xanthomonas citri | IFO 3835 |
| 10. | Xanthomonas physalidicola | IFO 13555 |
| 11. | Kluyvera citrophila | ATCC 21285 |
| 12. | Gluconobacter liquefaciens | ATCC 14835 |
| 13. | Gluconobacter deoxyacetonicus | IFO 3271 |
| 14. | Clostridium acetobutylicum | ATCC 824 |
| 15. | Comamonas terrigena | IFO 12685 |
| 16. | Corynebacterium tritici | IFO 12164 |
| 17. | Sarcina lutea | ATCC 9341 |
| 18. | Staphylococcus aureus | IFO 3060 |
| 19. | Spirillum methamorphum | IFO 12012 |
| 20. | Bacillus megaterium | ATCC 14945 |
| 21. | Pseudomonas melanogenum | ATCC 17808 |
| 22. | Pseudomonas aeruginosa | IFO 3451 |
| 23. | Flavobacterium sp. | ATCC 21429 |
| 24. | Brevibacterium cerinum | ATCC 15112 |
| 25. | Protaminobacter alboflavus | IFO 13221 |
| 26. | Proteus rettgeri | ATCC 9250 |
| 27. | Beneckea hyperoptica | ATCC 15803 |
| 28. | Micrococcus luteus | AHU 1427 |
| 29. | Mycoplana bullata | IFO 13267 |
| 30. | Mycoplana dimorpha | IFO 13213 |
| 31. | Rhodopseudomonas spheroides | ATCC 21286 |

For carrying out the optically selective deacylation reaction, the enzyme may be provided, more specifically, in any of the following forms:

1. The culture liquor of the microorganism or treated matter thereof;

2. Cell bodies recovered from the culture broth by centrifugation which may be washed with saline water (usually about 1%), buffer solution and the like, or as a cell suspension;

3. A disrupted cell suspension, i.e., a suspension of the cell bodies disrupted mechanically or chemically;

4. A cell free extract, i.e., a liquid obtained by removing the disrupted cell bodies from the disrupted cell suspension; or 5. A purified enzyme solution which is obtained by recovering the enzyme protein with ammonium sulfate from the cell free extract and subjecting the enzyme protein to gel filtration, ion-exchange cellulose column chromatography, ion-exchange sephadex column chromatography, and the like.

Cells or the purified enzyme immobilized by a conventional method may be used.

The reaction is carried out at a temperature of 0° to 50° C., preferably 20° to 45° C. and at a pH of 4 to 10 in an inactive solvent which does not affect the reaction.

As the solvent, water is most preferably used. In order to dissolve the substrate(s) or cephalosporin analog(s), organic solvents such as acetone, methanol, ethanol, N,N-dimethylformamide, dimethylsulfoxide, and the like may be used. It is effective to add phosphate buffer, Veronal buffer or citric acid buffer to control the pH in the reaction. Reaction time being influenced by the kind and concentration of enzymes, the kind and concentration of substrates, reaction temperatures or reaction pH, is generally 30 minutes to 24 hours. It is most preferable to terminate the reaction when the reaction ratio reaches a maximum.

The concentration of cells is preferably 1 to 50 mg by dry weight per 1 ml of the reaction solution. When a purified enzyme is used, it is appropriate to use the amount of the enzyme having the same activity as that of the dry cell. The substrate Compound [V] is used in an amount of 0.5 to 50 mg per 1 ml of the reaction solution.

In the event the microorganism utilized also produces an enzyme such as $\beta$-lactamase, esterase or the like, which tends to prevent the desired reaction, such microorganisms can be mutated by known techniques to obtain a mutant strain which has a reduced productivity of the undesirable enzyme. Alternatively, inhibitors of such enzymes may be added in the reaction system to raise the reaction ratio.

After the completion of the reaction, isolation of the desired compound is carried out by a conventional method employed in the isolation and purification of organic compounds from culture liquors such as absorption using various carriers, ion-exchange chromatography, gel filtration, liquid-liquid extraction, and the like.

Among the compounds represented by the general formula (I), the optically active compounds of the cephalosporin analogs represented by the general formula (I-3)

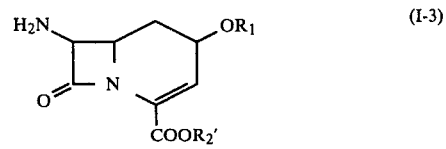

(wherein $R_1$ has the same significance as defined above, $R'_2$ represents a protective group of carboxylic acid and the hydrogens at the 6- and 7-positions have cis configuration) may also be obtained by the esterification of the optically active cephalosporin analogs represented by the general formula (I-4)

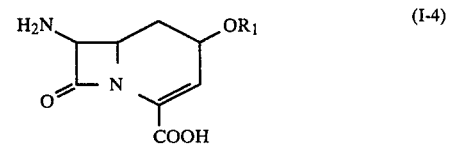

(wherein $R_1$ has the same significance as defined above, and the hydrogens at the 6- and 7-positions have cis configuration) by a conventional method, that is, the compound represented by the general formula (I-3')

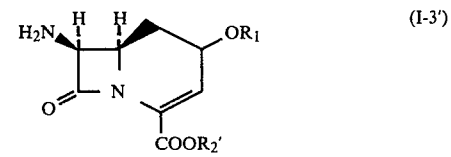

(wherein $R_1$ and $R'_2$ have the same significance as defined above) are obtained by the esterification of the compound represented by the general formula (I-4')

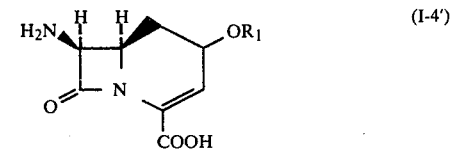

(wherein $R_1$ has the same significance as defined above) by a conventional method.

As the salts of the compounds of the invention, salts of the inorganic or organic bases, for example, the alkali metal salts such as sodium salts, potassium salts, etc., alkali earth metal salts such as magnesium salts, etc., ammonium salts, trimethylamine salts, triethylamine salts, pyridine salts, procaine salts, purine salts, lysine salts, arginine salts, etc. and salts of inorganic or organic acid, for example, hydrochloride, sulfate, carbonate, phosphate, formate, trifluoroacetate, malate, fumarate, etc. are exemplified.

Optically active compounds of the present invention, that is, Compound [I-1], themselves are expected to have antimicrobial activities and the acyl compounds of the optically active Compound [I] (Compound [I-1]) have much stronger antimicrobial activities than the acyl compounds of the corresponding optically inactive Compound [I]. Examples of such compounds and antimicrobial activities thereof are described in Reference Examples.

Methods of producing Compound [V] are described in the copending application Ser. No. (185,945). Examples of producing Compound [V] are described in Reference Example below.

The present invention is explained by the following Examples.

EXAMPLE 1

Preparation of (4S,6R,7S)-7-amino-4-hydroxy-1-azabicyclo[4,2,0]oct-2-en-8-on-2-carboxylic acid 1-1. Preparation of disrupted cell suspension (1) Cultivation of a microorganism having an ability of optically selective deacylation As the seed strain, *Kluyvera citrophila* ATCC 21285 [Biological properties are described in J. General Applied Microbiology 3, 28–31 (1957)] is used.

As the seed medium, an aqueous solution containing 1% polypeptone, 1% yeast extract, 0.5% meat extract, 0.5% sodium glutamate and 0.25% sodium chloride and adjusted at a pH of 7.0 with 5 N-NaOH is used. One loopful of the seed strain is inoculated into 10 ml of the seed medium in a large test tube (50 ml) and culturing is carried out at a temperture of 30° C. for 24 hours. The whole of the seed broth is inoculated into 300 ml of the culture medium in 2 l of an Erlenmeyer flask and culturing is carried out with shaking at a temperature of 30° C. The composition of the culture medium is the same as that of the seed medium.

(2) Preparation of disrupted cell suspension

After culturing for 24 hours, the culture broth is subjected to centrifugation to obtain cell bodies. The cells are washed twice with 50 ml of 0.9% saline solution and suspended in a concentration of 40 mg/ml by dry weight in 1/30 M phosphate buffer solution (pH 8.0).

1-2. Preparation of a substrate solution

In this step, 200 mg of (±)-cis-7β-phenylacetamido-4α-hydroxy-1-azabicyclo[4,2,0]oct-2-en-8-on-2-carboxylic acid obtained as in Reference Example 2 below is added into 9 ml of 1/30 M phosphate buffer (pH 8.0). Since the compound is not dissolved, 2 N-NaOH is added in a small portion and the mixture is again adjusted at a pH of 8.0 to dissolve the compound. Finally, deionized water is added to make 10 ml of a solution.

1-3. Enzyme reaction

In this step, 10 ml of the disrupted cell suspension mentioned above is added in 10 ml of a substrate solution and enzyme reaction is carried out at a temperature of 40° C. for 80 minutes. Time course of the reaction is illustrated in Table 1.

TABLE 1

| Reaction period (minutes) | The amount of Compound (I-1)* produced (mg/ml) | Yield (Mol ratio, %) |
|---|---|---|
| 10 | 0.8 | 12.5 |
| 20 | 1.3 | 20 |
| 40 | 1.8 | 29 |
| 60 | 2.1 | 33 |
| 80 | 2.2 | 35 |

*Compound (I-1) wherein $R_1$ is H and $R_2$ is H.

1-4. Isolation and Purification of the desired compound (a) After the completion of the reaction, cells are removed by centrifugation from the reaction solution. The supernatant is concentrated under reduced pressure and charged on a column (diameter: 0.88 cm, height: 70 cm) packed with 43 ml of Diaion HP-20AG (100–200 mesh, product of Mitsubishi Kasei Kogyo Co., Ltd.). Elution is carried out with deionized water and the desired compound is eluted from 36 ml to 45 ml of the eluate. The eluate are concentrated under reduced pressure and subjected to high speed liquid chromatography using TRI ROTAR (product of Nippon Bunko Co., Ltd.) and Shodex OH Pak B-804 (product of Showa Denko Co., Ltd.). Elution is carried out with water. Eluates are concentrated under reduced pressure and lyophilized to obtain 37.6 mg of a white powder. Properties of the product are as follows.

$IR\nu_{max}^{KBr}$ (cm$^{-1}$): 3530, 3190, 1746, 1620, 1550.

NMR (D$_2$O, with DSS as an internal standard)δ: 6.17(1H, d, J=5.4 Hz), 4.95(1H, d, J=5.4 Hz), 4.59(1H, m), 4.11(1H, m), 2.23(1H, m), 1.80(1H, m).

The properties of the product coincide well with those of the corresponding dl-compound. The value of optical rotation is $[\alpha]_D^{30°} = +24.2°$ (c=0.153, H$_2$O). It is assumed that the product is a mixture of the desired compound obtained by purifying as in Methods (b) and (c) and a trace amount of a dextrorotatory compound.

The compound shows a ninhydrin positive single spot at an Rf value of 0.38 on silica gel thin layer chromatography [thin layer plate Merck Art 5721 (product of E. Merck & Co.], solvent for development, ethanol:acetic acid:water=4:1:1]. The Rf value coincides with that of the optically inactive dl-compound.

(b) After the completion of the enzyme reaction carried out as in Example 1-1 to 1-3, cell bodies are removed from the reaction solution by centrifugation and the supernatant is concentrated under reduced pressure. The concentrate is charged on a column (diameter: 0.88 cm, height: 70 cm) packed with 43 ml of Diaion HP-20AG (product of Mitsubishi Kasei Kogyo Co., Ltd., 100–200 mesh). Elution is carried out with water. Eluted fractions (36 ml to 45 ml) containing the desired compound are again concentrated under reduced pressure. The concentrate is charged on a column (diameter: 0.88 cm, height: 33 cm) packed with 20 ml of Diaion WA-30-S (product of Mitsubishi Kasei Kogyo Co., Ltd.) which is in advance made acetic acid form by passing 40 ml of 0.5 N aqueous acetic acid through the column. After 20 ml of water is passed through the column to eliminate contaminants such as inorganic ions, 0.5 N aqueous acetic acid is passed through it. The desired product is eluted in the fractions (30 to 45 ml) of 0.5 N aqueous acetic acid. The fractions are lyophilized to obtain 32 mg of the desired product as pale yellow powder. Properties of the product are as follows and the product is identified as the acetate of the desired compound.

IR$\nu_{max}^{KBr}$ (cm$^{-1}$): 3400, 1805, 1760, 1745(sh), 1600, 1560(sh), 1410.

NMR (D$_2$O, with DSS as an internal standard)δ(ppm): 6.16(1H, d, J=5.4 Hz), 4.89(1H, d, J=5.4 Hz), 4.57(m, superimposed with the signal due to H$_2$O), 4.08(1H, m), 2.21(1H, m), 1.97(3H, s), 1.78(1H, m).

Optical rotation $[\alpha]_D^{20°} = -62.1°$ (c=0.16, 1M phosphate buffer, pH 7.0).

(c) Preparation of (4S, 6R, 7S)-7-amino-4-hydroxy-1-azabicyclo[4,2,0]oct-2-en-8-on-2-carboxylic acid (Alternative method):

(c-1) Preparation of (4S, 6R, 7S)-7-t-butoxycarbonylamino-4-hydroxy-1-azabicyclo[4,2,0]oct-2-en-8-on-2-carboxylic acid After the completion of the enzyme reaction carried out as in Example 1-1 to 1-3, cell bodies are removed from the reaction solution by centrifugation and the supernatant is concentrated under reduced pressure. The concentrate is charged on a column (diameter: 0.88 cm, height: 70 cm) packed with 43 ml of Diaion HP-20 (product of Mitsubishi Kasei Kogyo Co., Ltd., 100–200 mesh). Elution is carried out with water. Eluted fractions (36 ml to 45 ml) are combined, concentrated under reduced pressure and lyophilized to obtain 100 mg of a white powder. To the powder are added 1.0 ml of dioxane, 1.0 ml of water, 21 μl of triethylamine and 40 mg of S-t-butoxycarbonyl-4,6-dimethyl-2-mercaptopyridine and the mixture is stirred at room temperature for 4 days and at 40° C. for 17 hours. The reaction solution is concentrated under reduced pressure to reduce the volume to about half. The residue is washed with ethyl acetate three times and the pH of the water layer is adjusted to about 3 with 10% aqueous citric acid under ice cooling. After extracting with ethyl acetate five times, the ethyl acetate layer is washed with saturated saline solution twice, dried with anhydrous sodium sulfate and concentrated under reduced pressure to obtain 6.5 mg of white crystals. The product is identified as the desired compound based on the following properties.

IR$\nu_{max}^{KBr}$ (cm$^{-1}$): 3450, 3350, 1785, 1765, 1640, 1540.

NMR (CD$_3$OD)δ(ppm): 6.42(1H, d, J=5.4 Hz), 5.27 (1H, d, J=5.4 Hz), 4.41(1H, m), 3.95(1H, m), 2.3–1.2(2H, m), 1.46(9H, s).

Optical rotation $[\alpha]_D^{21°} = -38.2°$ (c=0.11, CH$_3$OH).

(c-2) Preparation of (4S, 6R, 7S)-7-amino-4-hydroxy-1-azabicyclo[4,2,0]oct-2-en-8-on-2-carboxylic acid In this process, 3 ml of anhydrous methylene chloride is added to 63 mg of (4S, 6R, 7S)-7-t-butoxycarbonylamino-4-hydroxy-1-azabicyclo[4,2,0]oct-2-en-8-on-2-carboxylic acid obtained as in Example c-1 and 3 ml of trifluoroacetic acid is added with stirring under ice cooling. The mixture is stirred at the same temperature as above for 3.5 hours. Thereafter, the reaction solution is concentrated under reduced pressure to obtain a brown oily product. The product is treated with ethyl ether to obtain 35 mg of a crude desired product as a yellow powder. The product is charged on a column packed with 50 ml of Diaion HP-20AG (product of Mitsubishi Kasei Kogyo Co., Ltd.) and elution is carried out with water. Fractions positive to ninhydrin color reaction are combined and concentrated under reduced pressure to obtain 31 mg (47.0%) of the trifluoroacetate of the desired compound. The product is identified as the trifluoroacetate of the desired compound based on the following properties.

IR$\nu_{max}^{KBr}$ (cm$^{-1}$): 3400, 1800, 1780, 1680, 1620.

NMR (D$_2$O)δ(ppm): 6.31(1H, d, J=5.4 Hz), 5.00(1H, d, J=5.4 Hz), 4.60(1H, m), 4.16(1H, m), 2.37–1.66(2H, m).

Optical rotation $[\alpha]_D^{21°} = -61.9°$ (c=0.0743, H$_2$O).

The compounds obtained in steps (b) and (c) behave exactly same as the compound in step (a) in thin layer chromatography under the same conditions.

EXAMPLE 2

Preparation of (4S, 6R, 7S)-7-amino-4-hydroxy-1-azabicyclo[4,2,0]oct-2-en-8-on-2-carboxylic acid (Alternative method)

(2-1) Preparation of immobilized enzyme

Cell bodies of *Kluyvera citrophila* ATCC 21285 cultivated in five 2 l-flasks as in Example 1-1 are suspended in 1/30 M phosphate buffer (pH 7.0) in a concentration of 40 mg/ml as dry weight. The cells are subjected to ultrasonic disintegration at 200 W for 2 minutes using ultrasonic disintegrator Model UR.200 P (product of Tomy Seiko Co., Ltd.). The disrupted cells are subjected to centrifugation to obtain a supernatant. After adding 1% (weight) of the sulfate of streptomycin, the supernatant solution is allowed to stand overnight. Nucleic acid is removed from the solution and ammonium sulfate is added in a concentration of 70% saturation to deposit enzyme proteins. The deposit is recovered by centrifugation and again dissolved in 50 ml of deionized water. The solution is subjected to dialysis for desalting. The enzyme solution is concentrated under reduced pressure to 10 ml and 0.5 ml of 1 M acetic acid-sodium acetate buffer (pH 5) is added. Separately 10 ml of Diaion WK-10 (product of Mitsubishi Kasei Kogyo Co., Ltd.) is pretreated in 1/20 M acetic acid-sodium acetate buffer (pH 5). The enzyme solution and WK-10 are mixed and the mixture is stirred at a temperature of 30° C. overnight. Thus, an immobilized enzyme is prepared.

(2-2) Reaction, isolation and purification of the desired compound

The immobilized enzyme (10 ml) mentioned above and 10 ml of a substrate solution prepared as in Example 1-2 are mixed in a large tube and stirred at a temperature of 40° C. for 2 hours. Reaction solution is subjected to decantation and purification as in Example 1-4. The product obtained shows almost same properties as those in Example 1.

Reference Example 1

Preparation of (±)-cis-7β-[2-(2-amino-4-thiazolyl)-2-syn-methoxyiminoacetamido]-4α-hydroxy-1-azabicyclo[4,2,0]oct-2-en-8-on-2-carboxylic acid

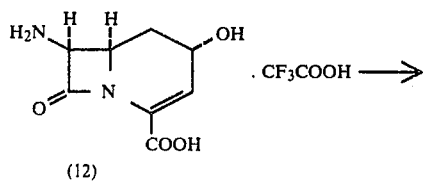

(12)

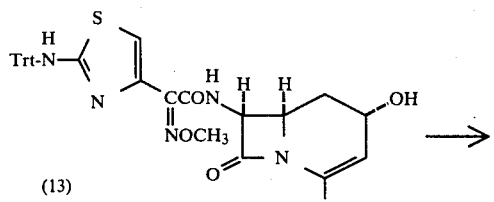

(13)

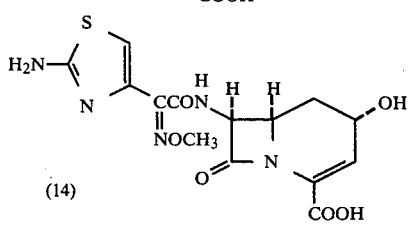

(14)

In this Example, 60 mg (0.203 m mole) of the trifluoroacetate of (±)-cis-7β-amino-4α-hydroxyl-1-azabicyclo[4,2,0]oct-2-en-8-on-2-carboxylic acid obtained as in the method described in Japanese Published Unexamined Patent Application No. 128591/79 is dissolved in a mixture of 1 ml of water and 1 ml of tetrahydrofuran and 56 μl of triethylamine is added to the solution. The mixture is identified as Reaction solution A. On the other hand, 125.7 mg (0.280 m mole) of 2-(2-tritylamino-4-thiazolyl)-2-syn-methoxyiminoacetic acid is dissolved in 1.2 ml of anhydrous methylenechloride and the solution is allowed to react under cooling on a dry-ice-carbon tetrachloride with stirring for 50 minutes after the addition of 39.3 μl of triethylamine and 55 mg (0.264 m mole) of phosphorous pentachloride. The reaction solution is concentrated under reduced pressure and to the residue 1 ml of anhydrous tetrahydrofuran is added to make an acid chloride solution. The acid chloride solution and 28 μl of triethylamine are added to Reaction solution A obtained above in three portions in 5 minutes. The mixture is allowed to react additionally for 35 minutes and adjusted to pH 2.5 with 10% citric acid. The solution is saturated with sodium chloride and extracted with ethyl acetate three times. The organic solvent layers are washed with saturated saline solution and dried with anhydrous sodium sulfate. After filtration and concentration, the residue is subjected to purification by silica gel chromatography (silica gel 15 g, solvent, methanol:chloroform=1:3) to obtain 185.5 mg of a crude acyl product. To 86 mg of the acyl product [Compound (13)] 3 ml of 50% acetic acid is added and the mixture is stirred at a temperature of 50° C. for 50 minutes. The mixture is cooled and the deposited triphenylcarbinol is removed by filtration. The filtrate is concentrated under reduced pressure to obtain a yellow glassy crude product. The product is subjected to purification using 8 ml of Diaion HP-20 (product of Mitsubishi Kasei Kogyo Co., Ltd.) and a solvent of methanol and water (1:9 to 2:1) to obtain 14.5 mg (44.3%) of the desired compound. Properties of the compound are as follows.

IR$\nu_{max}^{KBr}$ (cm$^{-1}$): 3450, 1775, 1670, 1635, 1550.

NMR (DMSO d$_6$-CD$_3$OD)δ: 9.28(1H, d, J=8.4 Hz), 7.07(2H, s), 6.75(1H, s), 6.27(1H, d, J=5.4 Hz), 5.56(2H, m), 2.77–2.04(2H, m).

The signal of —OCH$_3$ is superimposed with the signals due to the solvent.

Reference Example 2

Preparation of (±)-cis-7β-phenylacetamido-4α-hydroxy-1-azabicyclo[4,2,0]oct-2-en-8-on-2-carboxylic acid

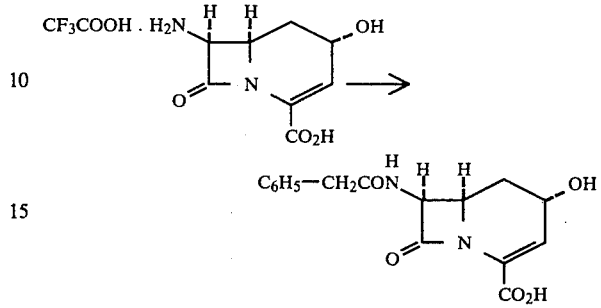

In this Example, 194.6 mg (0.623 m mole) of the trifuloroacetate of (±)-cis-7β-amino-4α-hydroxy-1-azabicyclo[4,2,0]oct-2-en-8-on-2-carboxylic acid is dissolved in a mixture of 3.1 ml of water and 6.2 ml of acetone and 209 mg (2.49 m mole) of sodium hydrogencarbonate are added to the solution. Then, 12.5 mg (0.810 m mole) of phenylacetylchloride in 2 ml of acetone is added dropwise to the mixture with stirring under ice cooling. 10.5 mg (0.068 m mole) and 17.6 mg (0.114 m mole) of phenylacetylchloride are added to the mixture after 1.5 and 2.5 hours, respectively. After 2 hours and 45 minutes, the reaction solution is concentrated under reduced pressure to remove acetone. Water (10 ml) and 1 N hydrochloric acid (1 ml) are added to the concentrate and the resulting solution is extracted three times with 20 ml of ethyl acetate. The ethyl acetate layer is washed with saturated saline solution, dried with anhydrous sodium sulfate, subjected to filtration and concentrated under reduced pressure.

The obtained brown oily product is triturated with ether, subjected to filtration and dried to obtain 120 mg (60.4%) of a powder of the desired compound. Properties of the product are as follows.

IR$\nu_{max}^{KBr}$ (cm$^{-1}$): 3400, 1780, 1670, 1640.

NMR (CD$_3$OD)δ: 7.27(5H, s), 6.39(1H, d, J=5.4 Hz), 5.46(1H, d, J=5.1 Hz), 4.37(1H, m), 4.01(1H, m), 3.57(2H, s), 2.0–1.1(2H, m).

Reference Example 3

Preparation of (±)-cis-7β-[(R)-2-t-butyloxycarbonylamino-2-phenylacetamido]-4α-hydroxy-1-azabicyclo[4,2,0]oct-2-en-8-on-2-carboxylic acid, t-butyl ester:

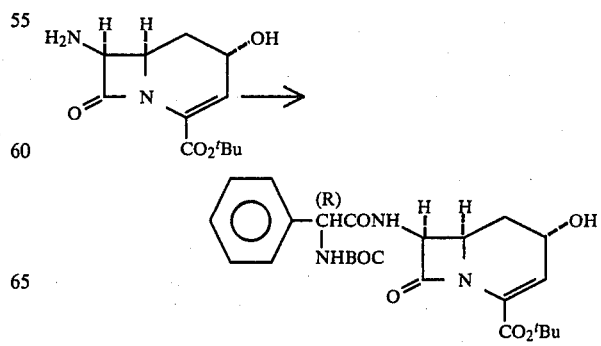

In this Example, 23.8 mg (0.095 m mole) of (R)-N-t-butyloxycarbonylphenylglycine is dissolved in 1 ml of anhydrous tetrahydrofuran, and 0.095 ml (0.095 m mole) of 1N-N-methylmorpholine-tetrahydrofuran and 0.095 ml (0.095 m mole) of 1N-isobutyl chloroformate-tetrahydrofuran are added at a temperature of −30° C. The mixture is stirred for 30 minutes and 20 mg (0.079 m mole) of (±)-cis-7β-amino-4α-hydroxy-1-azabicyclo[4,2,0]oct-2-en-8-on-2-carboxylic acid, t-butyl ester obtained as in the method described in Japanese Published Unexamined Patent Application No. 128591/79 in 1 ml of anhydrous methylene chloride is added thereto. The mixture is allowed to react at a temperature of −30° C. for 45 minutes and at 0° C. for 4 hours. The reaction mixture is then diluted with 5 ml of methylene chloride and is washed successively with water, 1N-HCl, 5%-NaHCO$_3$, water and saturated sodium chloride solution. The washing is dried with anhydrous sodium sulfate and concentrated to obtain 5 mg of a crude acylcompound. Purification by silica gel chromatography with 5 g of silica gel and a solvent of n-hexane and ethylacetate (15:1) is carried out to obtain 10 mg of the more polar isomer, 8 mg of the less polar isomer and 4 mg of a mixture thereof. Total yield 57%. Properties of the compounds are as follows.

The more polar isomer IR$\nu_{max}^{CHCl_3}$ (cm$^{-1}$): 3430, 1780, 1725(sh), 1717, 1697, 1630.

The less polar isomer IR$\nu_{max}^{CHCl_3}$ (cm$^{-1}$): 3430, 1780, 1722(sh), 1715, 1695, 1630.

Reference Example 4

Preparation of cis-7β-[(R)-2-phenylglycinamido]-4α-hydroxy-1-azabicyclo[4,2,0]oct-2-en-8-on-2-carboxylic acid

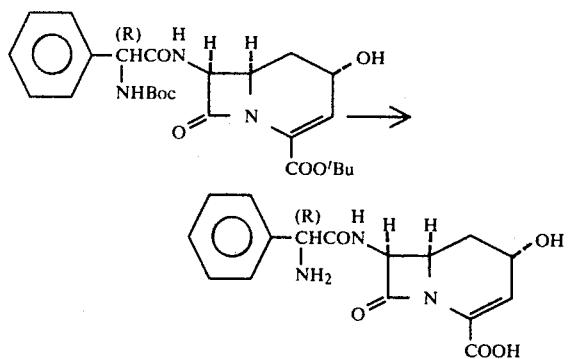

In this Example, 56 mg (0.118 m mole) of the less polar isomer of cis-7β-[(R)-2-t-butyloxycarbonylamino-2-phenylacetamido]-4α-hydroxy-1-azabicyclo[4,2,-0]oct-2-en-8-on-2-carboxylic acid, t-butyl ester obtained as in Reference Example 3 is dissolved in a mixture of 1 ml of anhydrous methylene chloride and 1 ml of anisole, and 2 ml of trifluoroacetic acid is added under ice cooling. The mixture is allowed to stand for 4 hours under ice cooling and then concentrated under reduced pressure. After adding dry benzene, the concentrate is again concentrated to obtain an oily product. The product is triturated with ether and the resulted precipitate is recovered by filtration to obtain 42.1 mg (80%) of a pale yellow powder of the trifluoroacetate of the desired compound. Properties of the product are as follows.

IR$\nu_{max}^{KBr}$ (cm$^{-1}$): 3485, 1780(sh), 1770, 1700(sh), 1685, 1635.

The obtained trifluoroacetate is dissolved in 2 ml of 1M-phosphate buffer (pH 7.0) and subjected to purification using 50 ml of Diaion HP-20AG and a solvent of water to water and methanol (9:1). The purified solution is lyophilized to obtain 28 mg (72%) of the desired compound. Properties of the product are as follows.

$[\alpha]_D^{24°} = -26.0°$ (c=0.53, H$_2$O).

IR$\nu_{max}^{KBr}$(cm$^{-1}$): 3480, 1780, 1770, 1680–1705, 1570–1650.

NMR (D$_2$O)δ: 7.52(5H, s), 6.03(1H, d, J=5.4 Hz), 5.5(1H, d, J=5.1 Hz), 5.21(1H, s), 4.28(1H, m), 4.06–3.85(1H, m), 1.76–0.99(2H, m).

Reference Example 5

Preparation of (±)-cis-7-azido-1-azabicyclo[4,2,0]-oct-2-en-4,8-dion-2-carboxylic acid, t-butyl ester

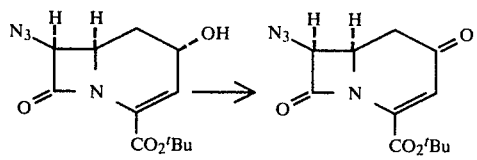

In this Example, 374 mg (2.760 m mole) of N-chlorosuccinimide is added to 7 ml of anhydrous toluene and the mixture is stirred in a stream of nitrogen at a temperature of −25° C. Then, 0.35 ml (4.766 m mole) of methylsulfide is added and the mixture is stirred for 10 minutes. After raised the temperature to −15° C., to the reaction mixture, 107 mg (0.382 m mole) of (±)-cis-7β-azido-4α-hydroxy-1-azabicyclo[4,2,0]oct-2-en-8-on-2-carboxylic acid, t-butyl ester prepared as in the method described in Japanese Published Unexamined Patent Application No. 128591/79 in 25 ml of anhydrous toluene is added and the mixture is stirred for 2.5 hours. A solution wherein 0.773 ml of anhydrous triethylamine is dissolved in 1.4 ml of anhydrous petroleum-ether is added to the reaction mixture in 2 minutes. The ice bath is removed and the mixture is stirred for 15 minutes. After adding 20 ml of ether, the solution is washed with a mixture of 3 ml of 5% hydrochloric acid and 20 ml of saturated saline solution and then washed with 5 ml of saturated saline solution twice. The ether layer is dried with anhydrous sodium sulfate and concentrated under reduced pressure to obtain 145.7 mg of a crude oily product of the desired compound. The product is subjected to silica gel chromatography using 10 g of Wako-gel C-200 and a solvent of n-hexane and ethyl acetate (2:1) to obtain 42.5 mg (0.153 m mole) of an oily product of the desired compound. Yield 40.1%. Properties of the product are as follows. IR$\nu_{max}^{CHCl_3}$ (cm$^{-1}$): 2125, 1802, 1740, 1698(sh), 1690.

NMR (CDCl$_3$)δ: 6.16(1H, s), 5.22(1H, d, J=5.5 Hz), 4.44 (1H, m), 3.10–2.48(2H, m), 1.55(9H, s).

REFERENCE EXAMPLE 6

Preparation of
(±)-cis-7β-azido-4β-hydroxy-1-azabicyclo[4,2,0]oct-2-en-8-on-2-carboxylic acid, t-butyl ester

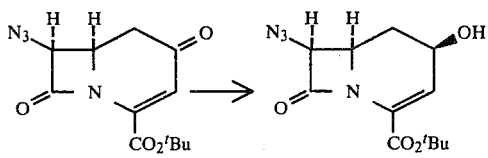

In this Example, 47 mg (0.169 m mole) of (±)-cis-7-azido-1-azabicyclo[4,2,0]-oct-2-en-4,8-dion-2-carboxylic acid, t-butyl ester prepared as in Reference Example 5 is dissolved in 1.6 ml of tetrahydrofuran containing 1% of water and the solution is stirred at a temperature of −40° C. Then, 32 mg (0.0845 m mole) of sodium borohydride is added and the mixture is stirred for 15 minutes. After adding a mixture of 10 ml of saturated saline solution and 1 ml of 10% hydrochloric acid, the mixture is extracted with 20 ml of ether twice. The ether layer is dried with anhydrous sodium sulfate and concentrated to dryness under reduced pressure to obtain 43.9 mg (0.157 m mole) of an oily product of the desired compound. Yield 92.7%. Properties of the product are as follows.

IR$\nu_{max}^{CHCl_3}$ (cm$^{-1}$): 3450, 2118, 1789, 1784(sh), 1729(sh), 1722, 1629, 1632(sh).

NMR (CHCl$_3$)δ: 6.20(1H, d, J=1.22 Hz), 4.86(1H, d, J=5.37 Hz), 4.62(1H, m), 3.98(1H, m), 2.45–1.65(3H, m), 1.53(9H, s).

Reference Example 7

Preparation of
(±)-cis-7β-amino-4β-hydroxy-1-azabicyclo[4,2,0]oct-2-en-8-on-2-carboxylic acid, t-butyl ester

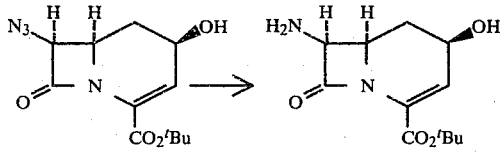

In this Example, 41.9 mg (0.149 m mole) of (±)-cis-7β-azido-4β-hydroxy-1-azabicyclo[4,2,0]oct-2-en-8-on-2-carboxylic acid, t-butyl ester obtained as in Reference Example 6 is dissolved in 1.5 ml of ethyl alcohol and 12 mg of 10% palladium-carbon is added. The mixture is stirred in a stream of hydrogen under ice cooling for 2 hours and 15 minutes. Then, after removing palladium-carbon by filtration, the filtrate is concentrated under reduced pressure and the concentrated residue is dissolved in 10 ml of ethyl acetate. The solution is extracted with 5 ml of 10% citric acid aqueous solution 4 times and the extract is washed with 5 ml of ethyl acetate. After adjusted to pH 8 with sodium carbonate, the washing is saturated with sodium chloride and extracted with 30 ml of ethyl acetate three times. The extract is washed with 30 ml of saturated saline solution, dried with anhydrous sodium sulfate and concentrated to dryness under reduced pressure to obtain 23.4 mg (0.092 m mole) of a pale yellow powder of the desired compound. Yield 61.6%. Properties of the compound are as follows.

IR$\nu_{max}^{CHCl_3}$ (cm$^{-1}$): 3430, 1774, 1734(sh), 1724, 1625(sh), 1618.

NMR (CDCl$_3$)δ: 6.18(1H, bs), 4.53(1H, m), 3.83(3H, m), 2.83(3H, bs), 2.20(1H, m), 1.51(3H, s).

Reference Example 8

Preparation of the trifluoroacetate of
(±)-cis-7β-amino-4β-hydroxy-1-azabicyclo[4,2,0]oct-2-en-8-on-2-carboxylic acid

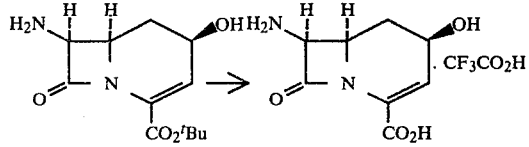

In this Example, 172.4 mg (0.678 m mole) of (±)-cis-7β-amino-4β-hydroxy-1-azabicyclo[4,2,0]oct-2-en-8-on-2-carboxylic acid, t-butyl ester obtained as in Reference Example 7 is dissolved in 8 ml of anhydrous methylene chloride and 8 ml of trifluoroacetic acid is added with stirring under ice cooling. The mixture is stirred at the same temperature for 1.5 hours. The reaction solvent is removed by distillation under reduced pressure and the resulted brown oily product is treated with ethyl ether to obtain 121.3 mg (0.389 m mole) of a yellow-brown powder. Yield 57.3%. Properties of the product are as follows.

IR$\nu_{max}^{KBr}$ (cm$^{-1}$): 3440, 1770, 1750(sh), 1700(sh), 1685.

Reference Example 9

Preparation of
(4S,6R,7S)-7-[2-(2-amino-4-thiazolyl)-2-syn-methoxyiminoacetamido]-4-hydroxy-1-azabicyclo[4,2,0]oct-2-en-8-on-2-carboxylic acid

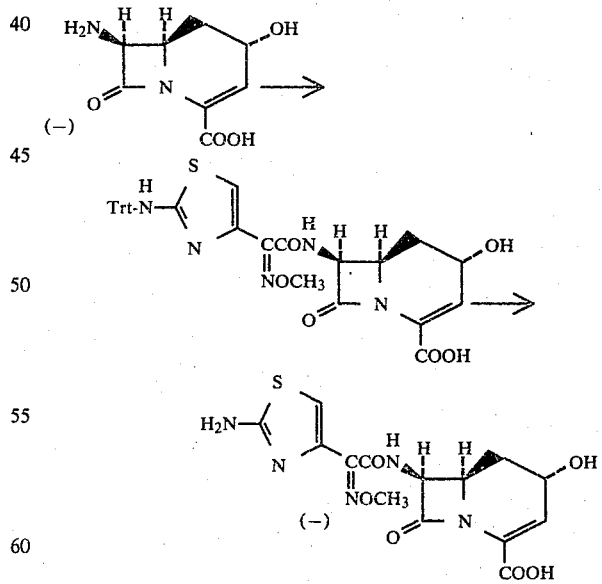

(9-1)

In this Example, 78.8 mg (0.178 m mole) of 2-(2-tritylamino-4-thiazolyl)-2-syn-methoxyiminoacetic acid is dissolved in 0.8 ml of anhydrous dichloromethane and 25 μl (0.178 m mole) of triethylamine is added at a temperature of −20° C. Then, after adding 37 mg (0.178 m mole) of phosphorus pentachloride, the mixture is allowed to react with stirring at a temperature of −20° C. for 40 minutes and concentrated under reduced pressure. The residue is dissolved in 40 ml of anhydrous tetrahydrofuran to make an acid chloride solution.

Separately, 34 mg (0.162 m mole) of the compound obtained as in Example 1-4-(a) is dissolved in a mixture of 1 ml of tetrahydrofuran and 1 ml of water and 79 μl (0.565 m mole) of triethylamine is added. The acid chloride solution prepared above is added dropwise to the solution with stirring under ice cooling and further 20 μl of triethylamine is added. The mixture is allowed to react for two hours and 45 minutes under ice cooling. Then, the mixture is adjusted to a pH of 2.0 with 10% hydrochloric acid and extracted twice with 10 ml of ethyl acetate. The ethyl acetate layers are washed with 10 ml of saturated saline solution, dried with saturated sodium sulfate and concentrated under reduced pressure to obtain 114 mg of a crude acyl compound. The product is dissolved in 10 ml of 50% acetic acid and stirred at a temperature of 50° C. for 30 minutes. The solution is cooled to room temperature and concentrated. The residue is dissolved in 1 ml of methanol. 20 ml of ether and 20 ml of n-hexane are added to the solution and the mixture is subjected to centrifugation to obtain a deposit. The deposit is lyophilized to obtain 51 mg of a solid. The solid is dissolved in a mixture of methanol and water (1:1). The solution is charged on a column packed with 30 ml of HP-20AG and elution is carried out with 40 ml of a mixture of water and methanol (10:1). 30 ml of a mixture of water and methanol (4:1) and 150 ml of a mixture of water and methanol (1:1). Fractions showing an Rf value of 0.3 by silica gel thin layer chromatography [plate: Merck Art. 5719 (product of E. Merck & Co.), solvent:butanol:acetic acid:water=4:1:1] are combined and concentrated under reduced pressure. The concentrate is dissolved in 20 ml of ether and 20 ml of n-hexane to obtain a precipitate. The precipitate is recovered by centrifugation and lyophilized to obtain 29.8 mg (yield 45.5%) as white crystals. Properties of the product are as follows. IRν$_{max}^{KBr}$ (cm$^{-1}$): 3450, 1775, 1670, 1635, 1550. NMR (DMSO d$_6$-CD$_3$OD)δ: 9.28(1H, d, J=8.4 Hz), 7.07(2H, s), 6.75(1H, s), 6.27(1H, d, J=5.4 Hz), 5.56(2H, m), 2.77-2.04(2H, m). The signal of —OCH$_3$ is superimposed with the signals due to the solvent.

$[\alpha]_D^{24°} = -32°$ (c=0.5, methanol).

(9-2)

For further purification, 200 mg of the crystals obtained as in step 9-1 is dissolved in 1 ml of methanol and 1 ml of hot water is added under heating at 50° C. The solution is allowed to stand at room temperature to obtain white crystals. The crytals obtained by repeating crystallization processes twice is washed with 1 ml of water and dried in vacuo at 45° C. for 12 hours. Yield 120 mg. The product is identified as the desired compound based on the following properties.

Melting point: The product turns purple at about 140' C. and gradually brown and decomposes at 176° to 178° C.

$[\alpha]_D^{19°} = -1°$ (c=0.9, methanol).

NMR (DMSO-d$_6$, 100M)δ: 13.1(1H, br), 9.25(1H, d, J=8.3 Hz), 7.20(2H, br), 6.76(1H, s), 6.25(1H, d, J=5.4 Hz), 5.48(1H, dd, J=8.3, 5.1 Hz), 5.26(1H, br), 4.30(1H, m), 3.84(3H, s), 1.43-2.05(2H, m), The signal of the proton at the 6-position is superimposed with the signal of —OCH$_3$ (δ3.84).

Elementary analysis Found C, 43.33%, H: 4.43%, N: 17.89%. Calculated as $C_{14}H_{15}N_5O_6$ S$\frac{1}{2}$H$_2$O C: 43.08%, H: 4.13%, N: 17.94%.

High resolutional mass spectrum The above crystals which are heated at 60° C. for 5 hours in N,O-bistrimethylsilylacetamido are provided as the sample.

Mass=669.23408 ($C_{26}H_{47}O_6N_5S$ Si$_4$).

(9-3) Alternative method (4S, 6R, 7S)-7-amino-4-hydroxy-1-azabicyclo[4,2,-0]oct-2-en-8-on-2-carboxylic acid obtained as in Example 1-4-b and 1-4-c is treated in the same manner as in Reference Example 9-1 and 9-2, whereby the same desired compound is obtained.

Reference Example 10

Antimicrobial activities of the compound obtained in Reference Example 9 are as follows. Heart Infusion Agar Dilution Method (pH 7.2) is used. Cefazolin and the compounds obtained in Reference Examples 1 and 4 are used as a control.

| Microorganism | MIC (μg/ml) | | | |
| --- | --- | --- | --- | --- |
| | A* | B* | C* | Cefazolin |
| Staphylococcus aureus 209-P | 3.12 | 12.5 | 3.12 | 0.02 |
| Staphylococcus aureus Smith | 12.5 | 25 | 25 | 0.78 |
| Staphylococcus epidermidis | 25 | 50 | 12.5 | 0.78 |
| Escherichia coli NIHJC-2 | 0.02 | 0.05 | 6.25 | 1.56 |
| Escherichia coli GN2411-5 | ≦0.01 | 0.02 | 3.12 | 0.78 |
| Escherichia coli Juhl | ≦0.01 | 0.05 | 3.12 | 1.56 |
| Klebsiella pneumoniae 8045 | ≦0.01 | 0.02 | 3.12 | 1.56 |
| Klebsiella pneumoniae Y-60 | ≦0.01 | 0.02 | 6.25 | 3.12 |
| Serratia marcescens T-26 | 0.02 | 0.4 | 100 | >100 |
| Serratia marcescens T-55 | 0.05 | 0.02 | 25 | >100 |
| Proteus mirabilis 1287 | 0.05 | 0.1 | 25 | 12.5 |
| Proteus vulgaris 6897 | ≦0.01 | 0.1 | 25 | 25 |
| Proteus morganii KY 4298 | ≦0.01 | 0.05 | 12.5 | >100 |
| Proteus rettgeri KY 4289 | ≦0.01 | <0.01 | 6.25 | 25 |
| Pseudomonas aeruginosa #1 | 0.78 | 12.5 | >100 | >100 |
| Pseudomonas aeruginosa 145 | 6.25 | 12.5 | >100 | >100 |
| Pseudomonas putida 264 | 0.02 | 0.02 | 12.5 | >100 |

*A The compound obtained in Example 9-2
*B The compound obtained in Reference Example 1
*C The compound obtained in Reference Example 4

What is claimed is:

1. A process for producing optically active compounds represented by the formula:

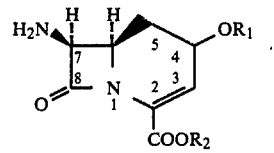

wherein R$_1$ represents a hydrogen, a lower alkyl group or a lower acyl group and R$_2$ represents a hydrogen or a protective group of carboxylic acid, which comprises reacting a compound represented by the formula

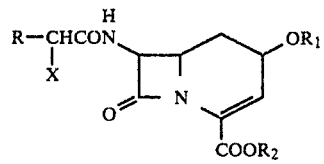

wherein R represents a substituted or unsubstituted unsaturated six-membered carbocycle or a substituted or unsubstituted heterocycle, X represents a hydrogen, an amino group, a hydroxy group or a lower alkyl group, $R_1$ and $R_2$ have the same significance as defined above, and the hydrogens at the 6- and 7-positions have cis configuration with an enzyme capable of selective optical deacylation and thereafter recovering said optically active compounds.

2. The process in claim 1, wherein said enzyme is obtained from a microorganism belonging to the genus Aeromonas, Achromobacter, Arthrobacter, Acetobacter, Alcaligenes, Escherichia, Xanthomonas, Kluyvera, Gluconobacter, Clostridium, Comamonas, Corynebacterium, Sarcina, Staphylococcus, Streptomyces, Spirillum, Bacillus, Pseudomonas, Flavobacterium, Brevibacterium, Protaminobacter, Proteus, Beneckea, Micrococcus, Myoplana and Rhodopseudomonas.

3. The process in claim 2, wherein said enzyme is provided to said reaction in the form of a purified enzyme solution, cell bodies recovered from a culture broth, a cell suspension, a disrupted cell suspension, a cell free extract, or a culture liquor of the microorganism.

4. The process in claim 3, wherein said enzyme is immobilized.

* * * * *